(12) United States Patent
Zheng

(10) Patent No.: US 10,398,222 B2
(45) Date of Patent: Sep. 3, 2019

(54) HEIGHT-ADJUSTABLE WORKSTATION

(71) Applicant: SHANGHAI TEAMMAX FURNITURE CO., LTD., Shanghai (CN)

(72) Inventor: Zaifeng Zheng, Shanghai (CN)

(73) Assignee: SHANGHAI TEAMMAX FURNITURE CO., LTD., Shanghai (CN)

(*) Notice: Subject to any disclaimer, the term of this patent is extended or adjusted under 35 U.S.C. 154(b) by 0 days.

(21) Appl. No.: 15/964,323

(22) Filed: Apr. 27, 2018

(65) Prior Publication Data
US 2018/0279769 A1 Oct. 4, 2018

Related U.S. Application Data

(63) Continuation of application No. PCT/CN2017/084934, filed on May 18, 2017.

(30) Foreign Application Priority Data

Mar. 30, 2017 (CN) .......................... 2017 1 0202461

(51) Int. Cl.
*A47B 9/10* (2006.01)
*G01G 19/44* (2006.01)
(Continued)

(52) U.S. Cl.
CPC .............. *A47B 9/10* (2013.01); *A47B 9/00* (2013.01); *A47B 21/02* (2013.01); *A47C 31/008* (2013.01);
(Continued)

(58) Field of Classification Search
CPC .. A47B 9/10; A47B 9/00; A47B 21/02; A47B 83/02; A47B 83/021; A47B 2200/0059; A47B 2200/0061; A47B 2200/0062
See application file for complete search history.

(56) References Cited

U.S. PATENT DOCUMENTS

2006/0208677 A1   9/2006 Schroder et al.
2016/0128467 A1*  5/2016 Sigal ........................ A47B 9/00
                                                700/275
(Continued)

FOREIGN PATENT DOCUMENTS

CN   203446828 U   2/2014
CN   203986987 U   12/2014
(Continued)

*Primary Examiner* — Daniel J Rohrhoff
(74) *Attorney, Agent, or Firm* — Im IP Law; C. Andrew Im; Chai Im

(57) ABSTRACT

An intelligent height-adjustable workstation includes a desktop and a seat cushion. The bottom of the desktop is supported by legs. Each of the legs is mounted with an electrical putter therein. The electrical putter is screw-fixed with the four corners of the bottom surface of the desktop. The underside of the desktop is mounted with an electrical putter control box. The electrical putter control box is mounted with a signal receiver therein. The bottom edge of the desktop is mounted with an electrical putter control panel connected to an external power supply. The seat cushion is mounted with a gravity sensor, a fiber optic sensor, a control box and a vibrator therein. The control box is mounted with a wireless signal generator and a lithium battery therein. The side of the seat cushion is mounted with a control panel. This improves work efficiency, reduces occurrence of occupational disease, alleviates sufferings.

5 Claims, 1 Drawing Sheet

(51) Int. Cl.
*A47B 21/02* (2006.01)
*A47C 31/00* (2006.01)
*A47B 9/00* (2006.01)
*A61B 5/02* (2006.01)
*A47B 83/02* (2006.01)

(52) U.S. Cl.
CPC .............. *G01G 19/44* (2013.01); *A47B 83/02* (2013.01); *A47B 2200/0059* (2013.01); *A47B 2200/0061* (2013.01); *A47B 2200/0062* (2013.01); *A61B 5/02* (2013.01)

(56) References Cited

U.S. PATENT DOCUMENTS

| | | | |
|---|---|---|---|
| 2016/0170402 A1* | 6/2016 | Lindstrom | A47B 9/00 700/275 |
| 2016/0309889 A1* | 10/2016 | Lin | A47B 9/00 |
| 2017/0354244 A1* | 12/2017 | Lee | A47B 9/20 |
| 2018/0020831 A1* | 1/2018 | Lenz | A47B 9/00 297/174 R |
| 2018/0090915 A1* | 3/2018 | Byrne | H02B 1/06 |
| 2019/0038017 A1* | 2/2019 | Platzer | A47B 21/02 |

FOREIGN PATENT DOCUMENTS

| | | | | |
|---|---|---|---|---|
| CN | 205197377 U | | 5/2016 | |
| CN | 205457104 U | | 8/2016 | |
| CN | 105919290 A | * | 9/2016 | |
| DE | 3027374 A1 | | 2/1982 | |
| DE | 102015002044 A1 | * | 8/2016 | ............... A47B 9/00 |

\* cited by examiner

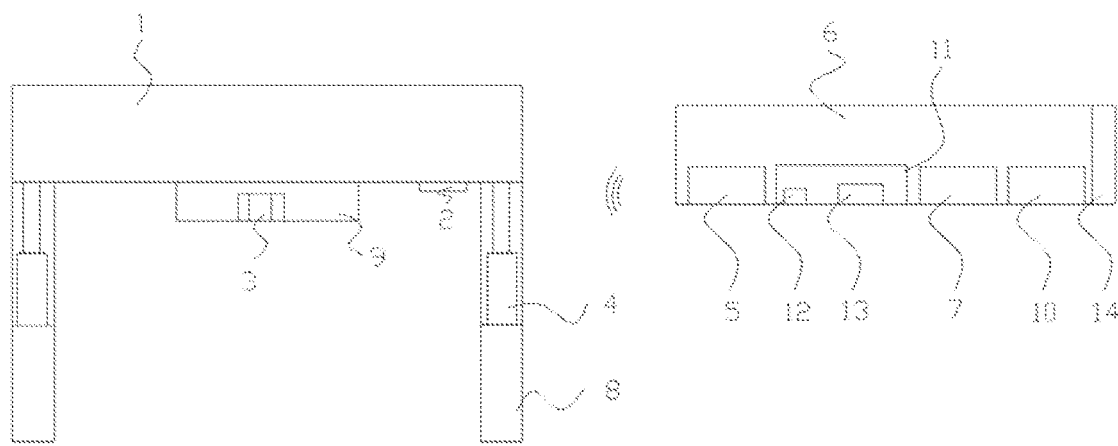

HEIGHT-ADJUSTABLE WORKSTATION

RELATED APPLICATIONS

This is a continuation application of the international application PCT/CN2017/084934 filed May 18, 2017, which claims the benefit of the Chinese application CN201710202461.0 filed Mar. 30, 2017, each of which is incorporated herein by reference in its entirety.

FIELD OF THE INVENTION

The present invention relates to a workstation including a desk and a chair, in particular, to an intelligent health height-adjustable workstation.

BACKGROUND OF THE INVENTION

The existing adjustable desks can achieve single-table rising or lowering by manual mechanical or electrical means to satisfy the "sitting-station interactive" work to ensure the health of the body. The office chair on the market only meets the basic adjustment functions, such as adjusting the height and depth of the seat. However, since the existing adjustable desks are controlled independently for rising and falling, actually when most people sit down and concentrate on their work, they will forget to stand up and rest intermittently. Therefore, when the body or leg feels unwell, it is found that several hours have passed. People often suffer from a series of office occupational diseases such as lumbar spondylosis, cervical spondylosis, and varicose veins due to sedentary habits, which endanger the health of the body. Thus, ordinary adjustable desks cannot really achieve the effect of "sit-seat interactive work."

OBJECTS AND SUMMARY OF THE INVENTION

The technical problem to be solved by the present invention is to provide an intelligent health adjustable workstation, because people often suffer from a series of office occupational diseases such as lumbar spondylosis, cervical spondylosis, and varicose veins due to sedentary habits, which endanger the health of the body, and the ordinary adjustable desks cannot really achieve the effect of "sit-seat interactive work."

In order to solve above technical problem, the present invention provides the following technical solutions:

The present invention discloses an intelligent health height-adjustable workstation comprising a desktop and a seat cushion; the bottom of the desktop is supported by legs and the desktop is connected with an external power supply; each of the legs is mounted with an electrical putter therein that can drive the desktop to move up and down in the vertical direction; the electrical putter is screw-fixed with the four corners of the bottom surface of the desktop; the underside of the desktop is mounted with an electrical putter control box; the electrical putter control box is mounted with a signal receiver therein; the side of the desktop is mounted with an electrical putter control panel; the seat cushion is mounted with a gravity sensor, a fiber optic sensor, a control box and a vibrator therein; the control box is mounted with a wireless signal generator and a lithium battery therein; the side of the seat cushion is mounted with a control panel.

As a preferred technical solution of the present invention, the gravity sensor is a pressure sensor, which is used to test the weight of the user.

As a preferred technical solution of the present invention, the electrical putter control panel is electrically connected with the signal receiver and the electrical putter, and the electrical putter control panel can control the opening and closing of the signal receiver connected therewith and control the raising and lowering of the electric putter.

As a preferred technical solution of the present invention, the lithium battery is electrically connected with the control panel and is charged by connecting with the external power supply; the control panel is electrically connected with the vibrator, the wireless signal generator, the gravity sensor and the fiber optic sensor; the control panel controls the vibration intensity and vibration time of the vibrator, and controls the opening and closing of the wireless signal generator; the fiber optic sensor can test human body's heartbeat and blood pressure and other physiological characteristics.

As a preferred technical solution of the present invention, the wireless signal generator is signally connected to the signal receiver.

Compared with the prior art, the beneficial effect of the present invention is that: nowadays, under the current situation of high intensity, high pressure and longer working hours, through reminding of sedentary automatically, collecting health data and analytic observation, wireless connection of the lift desk with the chair and automatic raising and lowering of the desk, a healthy "sitting station interactive work" may be really achieved, the work efficiency may be improved, the occurrence of occupational diseases in the office may be reduced, the pain caused by the disease may be decreased, and people's health, and reduce social and national medical costs may be lowered.

BRIEF DESCRIPTION OF FIGURES

In order to clearly illustrate the embodiments of the present invention or the technical solution in the prior art, the drawings required for the description of the embodiments or the prior art will be briefly introduced hereafter. In all the drawings, the similar elements or parts are generally denoted with similar drawing marks. In the drawings, the elements and parts are not necessarily drawn in an actual proportion.

FIG. 1 is a structural view of the present invention.

In FIGS.: 1. Desktop; 2. Electrical putter control panel; 3. Signal receiver; 4. Electrical putter; 5. Gravity sensor; 6. Seat cushion; 7. Fiber optic sensor; 8. Leg; 9. Electrical putter control box; 10. Vibrator; 11. Control box; 12. Wireless signal generator; 13. Lithium battery; 14. Control panel.

DETAILED DESCRIPTION OF THE EMBODIMENTS

The technical schemes of the embodiments of the present invention are clearly and completely described below with reference to the accompanying drawings in the embodiments of the present invention, it is apparent that the described embodiments are only a part of embodiments of the present invention, instead of all the embodiments. All other embodiments obtained by those skilled in the art based on the embodiments of the present invention without creative efforts shall fall within the protection scope of the present invention.

Referring to FIG. 1, the present invention discloses a technical solution: an intelligent height-adjustable workstation comprising a desktop 1 and a seat cushion 6; the bottom of the desktop 1 is supported by legs 8; each of the legs 8 is mounted with an electrical putter 4 therein; the electrical putter 4 is screw-fixed with the four corners of the bottom surface of the desktop 1; the bottom edge of the desktop 1 is mounted with an electrical putter control box 9 connected with an external power supply; the electrical putter control box 9 is mounted with a signal receiver 3 therein; the side of the desktop 1 is mounted with an electrical putter control panel 2; the seat cushion 6 is mounted with a gravity sensor 5, a fiber optic sensor 7, a control box 11 and a vibrator 10 therein; the control box 11 is mounted with a wireless signal generator 12 and a lithium battery 13 therein; the side of the seat cushion 6 is mounted with a control panel 14. The gravity sensor 5 is a pressure sensor. The electrical putter control panel 2 is electrically connected with the signal receive 3 and the electrical putter 4. The lithium battery 13 is electrically connected with the control panel 14, and the control panel 14 is electrically connected with the vibrator 10, the wireless signal generator 12, the gravity sensor 5 and the fiber optic sensor 7. The wireless signal generator 12 is signally connected to the signal receiver 3.

During operation, when a person sits on the seat cushion 6, he/she is detected by the gravity sensor 5 and the fiber optic sensor 7 inside the seat cushion 6, and the gravity sensor 5 detects the pressure and transmits the information to the control panel 14. Similarly, the fiber optic sensor 7 can detect human vital signs information (heartbeat, blood pressure, respiratory frequency) and transmit it to the control panel 14 as well. The control panel 14 will analyze the information upon receiving the information. The time on the control panel 14 may be firstly set by the user such that when the specified time is reached, the control panel 14 causes the vibrator 3 to vibrate and send the signal through the wireless signal generator 12. At this time, the signal receiver 3 can receive the signal. Then after receiving the signal from the signal receiver 3, the electrical putter control panel 2 starts the putter 4, and the table will automatically rise to force the person to stand. When the person sits down again, the gravity sensor 5 again detects the pressure information and passes the information to the control panel 14. Through the wireless signal generator 12 and the signal receiver 3, the signal can be transmitted to the electrical putter control panel 2. The electrical putter control panel 2 thus pushes the putter 4 to the original position. The mobile phone APP can also receive the signal information from the wireless signal generator 12 so as to display the dynamic vital signs information such as heartbeat and blood pressure on the mobile phone APP.

Nowadays, under the current situation of high intensity, high pressure and longer working hours, through reminding of sedentary automatically, collecting health data and analytic observation, wireless connection of the lift desk with the chair and automatic raising and lowering of the desk, a healthy "sitting station interactive work" may be really achieved, the work efficiency may be improved, the occurrence of occupational diseases in the office may be reduced, the pain caused by the disease may be decreased, and people's health, and reduce social and national medical costs may be lowered.

At last, it should be illustrated that the above various embodiments are only used to illustrate the technical schemes of the present invention without limitation; and despite reference to the aforementioned embodiments to make a detailed description for the present invention, the ordinary technical personnel in this field should understand: the described technical scheme in above various embodiments can be modified or the part of or all technical features can be equivalently substituted; while these modifications or substitutions do not make the essence of their corresponding technical schemes deviate from the scope of the technical schemes of the embodiments of the present invention, all of which should be contained within the scope of the claims and description of the present invention.

What is claimed is:

1. A height-adjustable workstation, comprising a desktop and a seat cushion, wherein:
   a bottom of the desktop is supported by legs;
   each of the legs is mounted with an electrical putter therein;
   the electrical putter is screw-fixed with four corners of a bottom surface of the desktop;
   an underside of the desktop is mounted with an electrical putter control box;
   the electrical putter control box is mounted with a signal receiver therein;
   a bottom edge of the desktop is mounted with an electrical putter control panel connected to an external power supply;
   the seat cushion is mounted with a gravity sensor, a fiber optic sensor, a control box and a vibrator therein;
   the control box is mounted with a wireless signal generator and a lithium battery therein; and
   a side of the seat cushion is mounted with a control panel.

2. The height-adjustable workstation in claim 1, wherein the gravity sensor is a pressure sensor.

3. The height-adjustable workstation in claim 1, wherein the electrical putter control panel is electrically connected to the signal receiver and the electrical putter.

4. The height-adjustable workstation in claim 1, wherein:
   the lithium battery is electrically connected to the control panel; and
   the control panel is electrically connected to the vibrator, the wireless signal generator, the gravity sensor and the fiber optic sensor.

5. The height-adjustable workstation in claim 1, wherein the wireless signal generator is signally connected to the signal receiver.

* * * * *